United States Patent
Schwartz

(10) Patent No.: US 9,861,836 B2
(45) Date of Patent: Jan. 9, 2018

(54) LESS INVASIVE METHODS FOR ABLATION OF FAT PADS

(75) Inventor: Yitzhack Schwartz, Haifa (IL)

(73) Assignee: Biosense Webster, Inc., Diamond Bar, CA (US)

(*) Notice: Subject to any disclaimer, the term of this patent is extended or adjusted under 35 U.S.C. 154(b) by 2057 days.

(21) Appl. No.: 11/154,367

(22) Filed: Jun. 16, 2005

(65) Prior Publication Data

US 2006/0287648 A1    Dec. 21, 2006

(51) Int. Cl.
| | | |
|---|---|---|
| *A61B 18/04* | (2006.01) | |
| *A61N 7/02* | (2006.01) | |
| *A61B 18/14* | (2006.01) | |
| *A61B 34/20* | (2016.01) | |
| *A61B 17/22* | (2006.01) | |
| *A61B 18/18* | (2006.01) | |
| *A61B 18/24* | (2006.01) | |
| *A61B 18/00* | (2006.01) | |
| *A61B 34/10* | (2016.01) | |
| *A61B 90/00* | (2016.01) | |

(52) U.S. Cl.
CPC .......... *A61N 7/022* (2013.01); *A61B 18/1492* (2013.01); *A61B 34/20* (2016.02); *A61B 17/2202* (2013.01); *A61B 18/18* (2013.01); *A61B 18/24* (2013.01); *A61B 2018/00363* (2013.01); *A61B 2018/00577* (2013.01); *A61B 2034/105* (2016.02); *A61B 2034/2051* (2016.02); *A61B 2090/378* (2016.02); *A61N 7/02* (2013.01)

(58) Field of Classification Search
CPC ................. A61B 2018/00363; A61B 18/1492
USPC ....... 606/13–14, 41; 607/1–2, 115, 119, 122
See application file for complete search history.

(56) References Cited

U.S. PATENT DOCUMENTS

| | | | | |
|---|---|---|---|---|
| 5,568,809 | A | | 10/1996 | Ben-haim |
| 6,053,873 | A | * | 4/2000 | Govari et al. ................ 600/505 |
| 6,292,695 | B1 | * | 9/2001 | Webster et al. ............... 607/14 |
| 6,511,500 | B1 | | 1/2003 | Rahme |
| 6,716,166 | B2 | | 4/2004 | Govari |
| 6,773,402 | B2 | | 8/2004 | Govari et al. |
| 6,802,857 | B1 | * | 10/2004 | Walsh et al. ................ 623/1.15 |
| 6,997,924 | B2 | | 2/2006 | Schwartz et al. |

(Continued)

OTHER PUBLICATIONS

Chen-Wang Chiou et al, Selective Vagal Denervation of the Atria Eliminates Heart Rate Variability and Baroreflex Sensitivity While Preserving Ventricular Innervation, Jul. 1998, American Heart Association, vol. 98, 360-367.*

(Continued)

*Primary Examiner* — Joseph Stoklosa
*Assistant Examiner* — Sean W Collins
(74) *Attorney, Agent, or Firm* — Louis J. Capezzuto

(57) ABSTRACT

Epicardial fat pad ablation is conducted using a catheter inserted through the chest wall, using ultrasound ablation, or using a catheter fitted with a directional ultrasound transducer and capable of being aligned with the epicardium. The epicardial fat pad locations are determined using noninvasive imaging methods, or using electrical maps. These locations are then displayed on maps or images of the heart, and thus targeted for minimally invasive or non invasive therapy. The methods of the present invention are less invasive than conventional methods of ablation, and permit flexible access to substantially any point on the epicardium.

15 Claims, 4 Drawing Sheets

(56) References Cited

U.S. PATENT DOCUMENTS

| | | | |
|---|---|---|---|
| 7,156,816 B2 | 1/2007 | Schwartz et al. | |
| 7,245,967 B1* | 7/2007 | Shelchuk | 607/14 |
| 7,308,297 B2* | 12/2007 | Reddy et al. | 600/407 |
| 7,678,104 B2* | 3/2010 | Keidar | 606/27 |
| 7,715,915 B1* | 5/2010 | Ryu et al. | 607/9 |
| 7,813,785 B2* | 10/2010 | Okerlund et al. | 600/425 |
| 7,826,899 B1* | 11/2010 | Ryu et al. | 607/14 |
| 8,060,197 B2* | 11/2011 | Ben-David et al. | 607/5 |
| 8,066,699 B2* | 11/2011 | Keidar | 606/27 |
| 8,204,591 B2* | 6/2012 | Ben-David et al. | 607/14 |
| 8,731,663 B2* | 5/2014 | Bianchi et al. | 607/14 |
| 8,909,337 B2* | 12/2014 | Moffitt et al. | 607/9 |
| 2002/0111615 A1* | 8/2002 | Cosman et al. | 606/41 |
| 2002/0120304 A1* | 8/2002 | Mest | 607/14 |
| 2003/0078644 A1* | 4/2003 | Phan | 607/119 |
| 2003/0079753 A1* | 5/2003 | Vaska et al. | 128/898 |
| 2004/0015106 A1* | 1/2004 | Coleman | 601/3 |
| 2004/0054363 A1* | 3/2004 | Vaska et al. | 606/27 |
| 2004/0162507 A1 | 8/2004 | Govari | |
| 2004/0162550 A1 | 8/2004 | Govari et al. | |
| 2005/0015079 A1* | 1/2005 | Keider | 606/27 |
| 2005/0033137 A1* | 2/2005 | Oral et al. | 600/374 |
| 2005/0090820 A1* | 4/2005 | Cornelius et al. | 606/41 |
| 2005/0101946 A1* | 5/2005 | Govari et al. | 606/33 |
| 2005/0119704 A1* | 6/2005 | Peters et al. | 607/3 |
| 2005/0197675 A1* | 9/2005 | David et al. | 607/9 |
| 2005/0261672 A1* | 11/2005 | Deem et al. | 606/41 |
| 2005/0267542 A1* | 12/2005 | David et al. | 607/17 |
| 2006/0200219 A1* | 9/2006 | Thrope et al. | 607/145 |
| 2006/0206159 A1* | 9/2006 | Moffitt et al. | 607/37 |
| 2006/0287648 A1* | 12/2006 | Schwartz | 606/27 |
| 2007/0038251 A1* | 2/2007 | Pachon Mateos et al. | 607/2 |
| 2007/0156185 A1* | 7/2007 | Swanson et al. | 607/2 |
| 2008/0004662 A1* | 1/2008 | Peters et al. | 607/3 |
| 2008/0147130 A1* | 6/2008 | Rom | 607/3 |
| 2008/0161894 A1* | 7/2008 | Ben-David et al. | 607/116 |
| 2010/0305634 A1* | 12/2010 | Moffitt et al. | 607/5 |
| 2012/0053510 A1* | 3/2012 | Peters et al. | 604/20 |
| 2012/0179216 A1* | 7/2012 | Moffitt et al. | 607/4 |

OTHER PUBLICATIONS

Wallick et al., "Separate Parasympathetic Control of Heart Rate and Atrioventricular Conduction of Dogs," Am. Phys. Society, 1990; 259(28):H536-H542.*

Chiou CW, Eble JN, Zipes DP. "Efferent Vagal Innervation of the Canine Atria and Sinuses and Atrioventricular Nodes," Circulation, 1997;95:2573-2584.*

Soejima Kyoko et al: "Subxiphoid Surgical Approach for Epidardial Catheter-Based Mapping and Ablation in Patients With Prior Cardiac Surgery or Difficult Pericardial Access"; Circulation, Sep. 7, 2004; pp. 1197-1201; vol. 110, No. 10.

Chiou C.W. et al: "Selective Vagal Denervation of the Atria Eliminates Heart Rate Variability and Baroreflex Sensitivity While Preserving Ventricular Innervation"; Circulation, Jul. 18, 1998, pp. 360-368; vol. 98, No. 4.

Hou, Yinglong, M.D. et al. "Ganglionated Plexi Modulate Extrinsic Cardiac Autonomic Nerve Input", Journal of the American College of Cardiology, vol. 50, No. 1, 2007.

Nakagawa, Hiroshi, M.D. PhD, et al. "Localization of Left Atrial Autonomic Ganglionated Plexuses Using Endocardial and Epicardial High Frequency Stimulation in Patients with Atrial Fibrillation", Heart Rhythm, vol. 2, No. 5, AB6-1May Supplement 2005.

Jackman et al. *Catheter Ablation of Cardiac Autonomic Nerves for Prevention of Vagal Atrial Fibrillation*, Circulation. 2000;102:2774-2780.

Chinese Official Action dated Jan. 14, 2013 from related application CN 200610092815.2 together with an English language translation.

Pappone C. et al., "Pulmonary Vein Denervation Enhances Long-Term Benefit After Circumferential Ablation for Paroxysmal Atrial Fibrillation", Circulation 109:327-334 (Jan. 27, 2004).

* cited by examiner

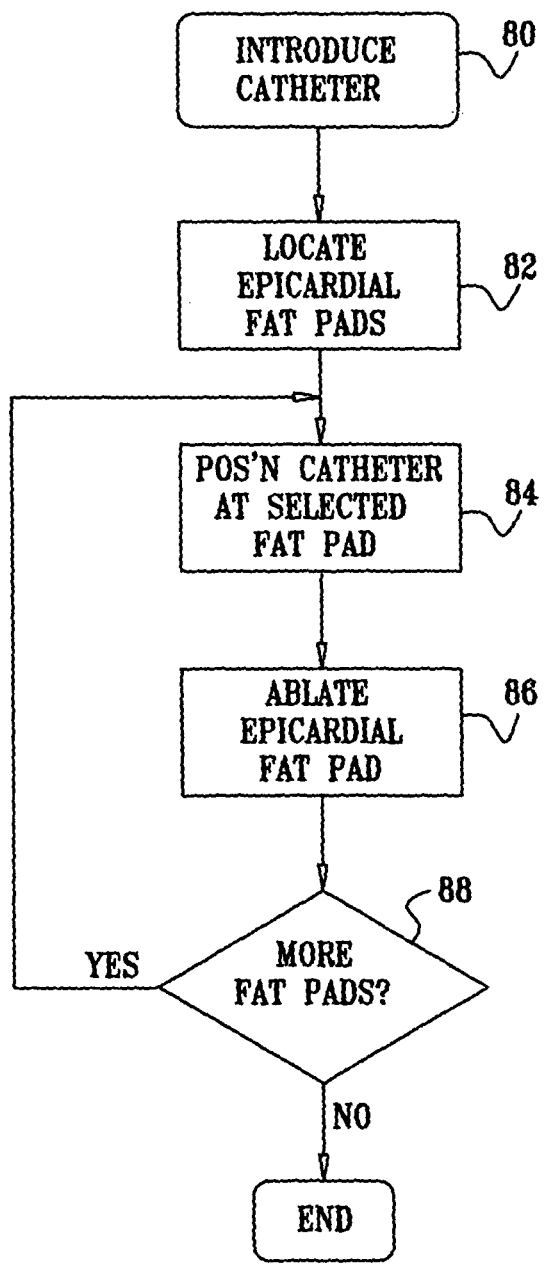

LESS INVASIVE METHODS FOR ABLATION OF FAT PADS

BACKGROUND OF THE INVENTION

Field of the Invention

This invention relates to control of cardiac arrhythmias. More particularly, this invention relates to minimally invasive methods for modifying the effects of the autonomic nervous system on the heart by denervation of epicardial fat pads.

Description of the Related Art

Innervation of the heart by the parasympathetic nervous system has a marked influence on aspects of the heart rhythm, and inter alia on atrial fibrillation. Recent research has demonstrated that parasympathetic ganglia are located in discrete epicardial fat pads:

The RPV fat pad, situated at the junction of the right atrium (RA) and right pulmonary veins (RPV), provides direct vagal inhibition of the sinoatrial (SA) node.

The IVC-ILA fat pad, situated at the junction of the inferior vena cava (IVC) and the inferior left atrium (ILA), selectively innervate the atrioventricular (AV) nodal region and regulate AV conduction.

The SVC-AO fat pad, situated between the medial superior vena cava (SVC) and aortic root superior to the right pulmonary artery, connects to vagal fibers projecting to both atria and to the IVC-ILA and PV fat pads.

It is known that individuals having a high level of vagal tone are predisposed to supraventricular arrhythmias, particularly atrial fibrillation. Ablation of epicardial fat pads has been found to affect vagally mediated atrial fibrillation. For example, in the document *Catheter Ablation of Cardiac Autonomic Nerves for Prevention of Vagal Atrial Fibrillation*, Jackman et al., Circulation 2000; 102:2774-2780, transvascular radiofrequency (RF) ablation of cardiac autonomic nerves for prevention of vagal atrial fibrillation in dogs is described, using an ablation catheter in the right pulmonary artery and or superior or inferior vena cava. A catheter that can be used for this purpose is described in commonly assigned U.S. Pat. No. 6,292,695 to Webster et al, which is herein incorporated by reference.

Surgical denervation of the fat pads has also been described.

The methods of parasympathetic denervation that are described in the literature generally involve surgical or transvascular approaches. There remains a need for improved, less invasive methods of denervating epicardial cardiac fat pads for prevention and treatment of supraventricular arrhythmias.

SUMMARY OF THE INVENTION

The present invention is based on the realization that because the fat pads that contain many of the parasympathetic ganglia are located on the epicardium, they are amenable to minimally invasive ablative techniques.

In embodiments of the invention, epicardial ablation is conducted using a catheter inserted through the chest wall. The catheter has transducers for directing laser energy, microwave energy or ultrasound energy toward target tissue.

Epicardial fat pad locations are determined using noninvasive imaging methods, i.e., cardiac CT or MR imaging, cardiac neurotransmission imaging using SPECT and PET or can be found using epicardial electrical maps. These locations are then displayed on maps or images of the heart, and thus targeted for minimally invasive or noninvasive therapy. The methods of the present invention are less invasive than conventional methods of ablation, and permit flexible access to substantially any point on the epicardium.

The invention provides a method for ablating epicardial tissue within a body of a subject, which is carried out by inserting a probe into the pericardial cavity, locating epicardial target tissue in the pericardial cavity for ablation thereof, disposing the probe in proximity to the target tissue, and directing sufficient energy from the probe preferentially toward the target tissue to ablate neural structures therein.

One aspect of the method includes orienting the probe with respect to the target tissue so as to maximize energy transfer from the probe to the target tissue.

According to yet another aspect of the method, orienting the probe includes sensing location and orientation information of the probe, and moving the probe responsively to the information.

According to another aspect of the method, the energy includes ultrasound energy. The ultrasound energy may be focused onto the target tissue.

According to a further aspect of the method, the energy is laser energy.

According to yet another aspect of the method, the energy is microwave energy.

According to still another aspect of the method, the target tissue is an epicardial fat pad.

According to an additional aspect of the method, the target tissue includes an epicardial ganglion that is external to an epicardial fat pad.

In still another aspect of the method, the probe includes a resonant circuit, and the method is further carried out by generating radiofrequency energy at a site remote from the resonant circuit at the circuit's resonant frequency, causing the resonant circuit to re-radiate energy toward the target tissue.

The invention provides a system for minimally invasive ablation of epicardial tissue of a heart of a living body, including a probe, which has a distal end configured for insertion into the pericardial cavity of the body. The probe has an exposed front surface and a back surface, and includes in proximity to the distal end at least one position sensing device and a transducer disposed so as to transmit energy directionally from the front surface to epicardial target tissue.

According to an additional aspect of the system, the probe includes a resonant circuit, the system further including a plurality of radiofrequency transmitters operative for generating radiofrequency energy at a site remote from the resonant circuit at the circuit's resonant frequency, causing the resonant circuit to re-radiate energy toward the target tissue.

The invention provides a system for minimally invasive ablation of epicardial tissue of a heart of a living body, including a first probe, having a first distal end configured for insertion into a pericardial cavity of the body, the first probe including in proximity to the first distal end at least one position sensing device. The system includes a second probe, which has a second distal end and having a transducer for delivery of energy to target tissue on the epicardial surface of the heart. The second probe is exchangeable with the first probe. The system further includes a source of the energy, which is coupled to the transducer, a processor, alternatively coupled to the first probe for determining position coordinates of the first distal end relative to the epicardial surface, using the position sensing device, and to the second probe. The processor is further adapted to control the source of the energy. The system includes a display, controlled by the processor, for displaying locations of the first probe and the second probe relative to the epicardial surface of the heart.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein:

FIG. 4 is a flow chart of a method of ablation of epicardial neural structures in accordance with a disclosed embodiment of the invention.

DETAILED DESCRIPTION OF THE INVENTION

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Embodiment 1

Figure 1:
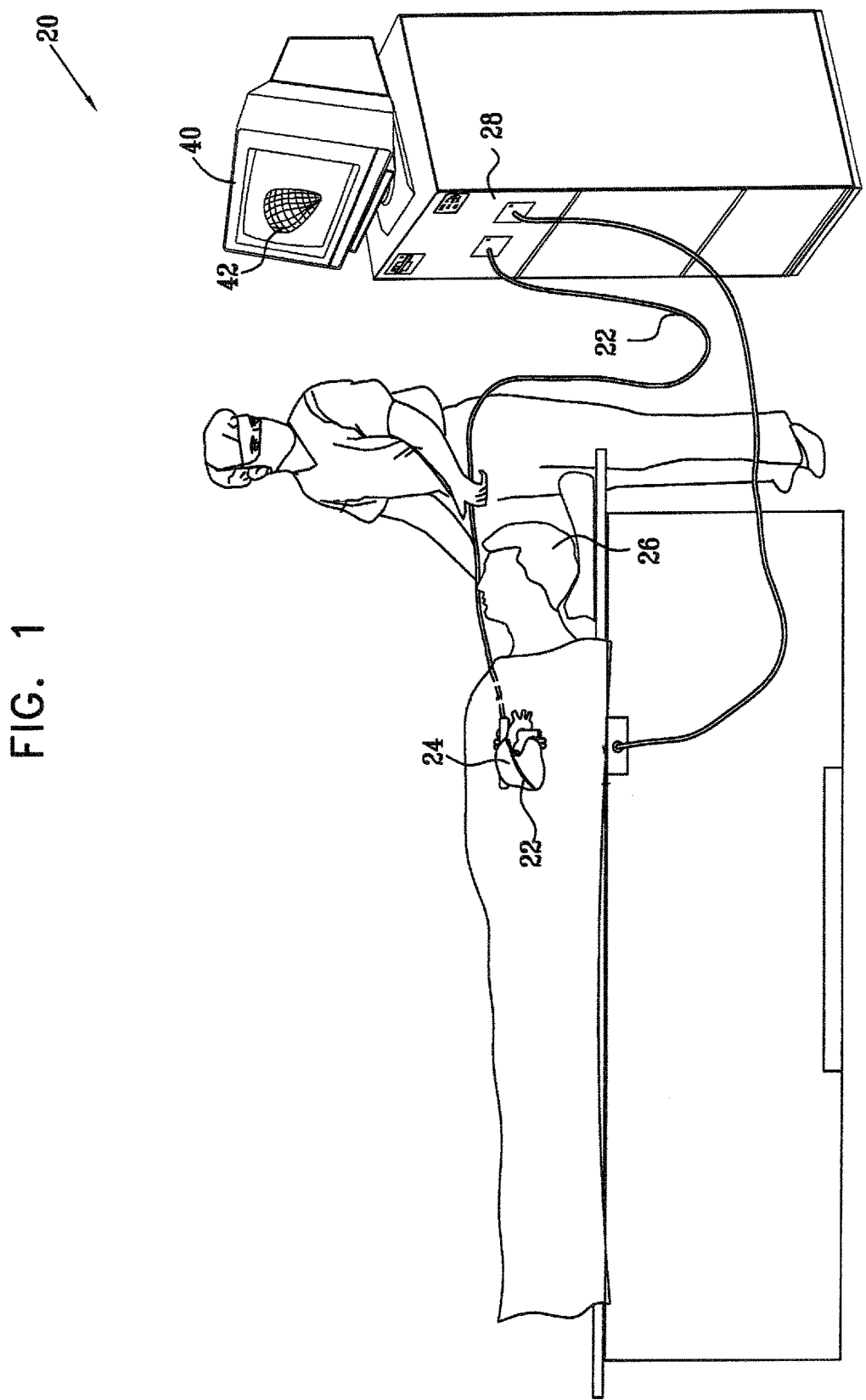
FIG. 1 is a schematic illustration of an ablation system, which is constructed and operative in accordance with a disclosed embodiment of the invention.

Turning now to the drawings, reference is initially made to FIG. 1, which is an illustration of a system 20, which is constructed and operative in accordance with a disclosed embodiment of the invention. The system 20 is used in determining the position of a probe, for the acquisition of anatomic and electrical data, and for tissue ablation using a catheter 22, which is percutaneously inserted into the pericardial cavity that includes a heart 24 of a subject 26. The distal tip of the catheter 22 comprises one or more electrodes, and in some embodiments includes one or more ablation transducers, e.g., ultrasound transducers. The electrodes and transducers are connected by wires through the insertion tube of the catheter 22 to a control unit 28. The control unit 28 determines position coordinates of the catheter 22 relative to the epicardial surface of the heart 24. The control unit drives a display 40, which shows the catheter position inside the body. The control unit 28 also drives the ablation transducers, which are located generally at the tip of the catheter 22. The catheter 22 is used in generating anatomic images 42 or even an electrical map, wherein the electrodes on the catheter are used alternately for position sensing and for ablation.

The system 20 can be the Carto® Navigation System, available from Biosense Webster, Inc., 3333 Diamond Canyon Road, Diamond Bar, Calif. 91765, configured for use with suitable epicardial location and/or ablation catheters. Using this system, the entire procedure can be carried out in a single session without disconnecting the subject 26 from the system.

Figure 2:
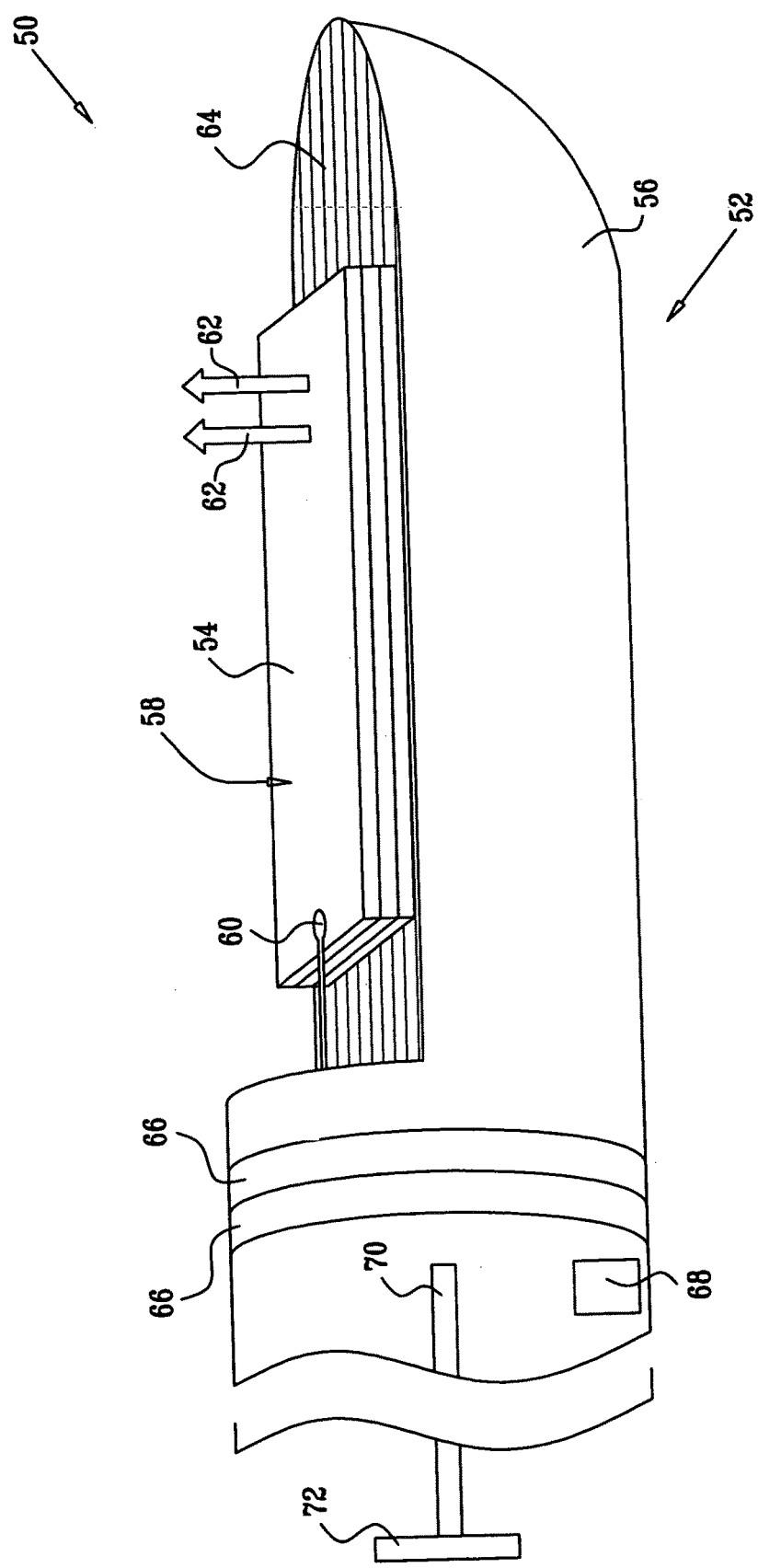
FIG. 2 is a perspective view of the distal end of a catheter for use in the system shown in FIG. 1.

Reference is now made to FIG. 2, which is a perspective view of a tip 50 of a catheter, which is suitable for use as the catheter 22 (FIG. 1). The catheter is described in commonly assigned application Ser. No. 10/621,988 filed Jul. 17, 2003, which is herein incorporated by reference. However, a brief description will facilitate understanding of the present invention. An exposed section 52 at the tip 50 ranges from about 2 mm to about 4 mm in length, and includes an ultrasound transducer 54. The exposed section 52 has a curved outer back surface 56 and a flat front surface 64, which includes a cut out region 58, on which the transducer 54 is mounted. A wire 60 connects the transducer 54 with an ultrasonic actuator (not shown). The energy output of the transducer 54 is directional, being transmitted away from and generally perpendicular to the exposed surface of the transducer 54, as indicated by arrows 62. In operation, the tip 50 is positioned so that when a surface 64 carrying the transducer 54 lies flat against the epicardium, ultrasonic energy is preferentially transmitted from the transducer 54 in the direction of the apposed epicardium. The catheter is provided with position sensors 66 for sensing the location and orientation of the tip 50 with respect to the epicardial surface, and a temperature sensor 68, which is useful in assessing the progress of an ablation operation. The control unit 28 (FIG. 1) is capable of sensing and displaying the orientation of the tip 50 as well as its location responsively to signals from the position sensors 66.

A deflection wire 70 is provided within the catheter for deflecting its distal portion. The deflection wire 70 is fixedly anchored near the tip 50, and is attached to a control handle 72. The deflection wire 70 is used to manipulate the catheter so as to align the exposed section 52 relative to a desired direction of energy emission.

Embodiment 2

In alternative embodiments of the system 20, location information is first prepared as a map or an image. The location information and the ablation are performed at different times, using exchangeable catheters typically during a single session with the subject 26. In such embodiments a first catheter contains position sensors and a second catheter contains at least one transducer that is used for tissue ablation, as well as components of a location and mapping system enabling its position to be identified.

The system 20 may be adapted, mutatis mutandis, to employ the catheters disclosed in commonly assigned U.S. Pat. No. 6,716,166 or U.S. Pat. No. 6,773,402 for mapping the surface of the heart, which are herein incorporated by reference, as the catheter 22.

Referring again to FIG. 1, following identification of the epicardial fat pads, the catheter disclosed in copending application Ser. No. 10/245,613, which is herein incorporated by reference, can be used for ablation as the catheter 22. This catheter employs laser energy, and a laser source (not shown) is controlled by the control unit 28.

Embodiment 3

Embodiment 3 is similar to embodiment 2, except that a non-directional ultrasound catheter is employed as the catheter 22 (FIG. 1). This can be the catheter disclosed in copending application Ser. No. 10/304,500, which is herein incorporated by reference. Microwave ablation catheters are also effective.

Embodiment 4

In this embodiment, a probe employing microwave energy as the ablation source is used as the catheter 22 (FIG.

1). A suitable probe and microwave generator, the FLEX 4™ system, are available from Guidant Corporation, 111 Monument Circle, #2900, Indianapolis, Ind. 46204-5129, Embodiment 5

In this embodiment, a probe employing high intensity focused ultrasound energy (HIFU) is used as the catheter 22 (FIG. 1), as described in U.S. Patent Application Publication Nos. 2004/0162507 and 2004/0162550, of common assignee herewith, and herein incorporated by reference. A suitable probe and control is commercially available as the Epicor™ Cardiac Ablation System, available from St. Jude Medical, One Lillehei Plaza St Paul Minn. 55117-9913. Using this system, a simplified Cox maze procedure can be performed to eradicate target tissue as described above. Notably, it is not necessary to arrest the heart, nor to resort to cardiopulmonary bypass.

Embodiment 6

This embodiment is similar to Embodiment 5. The catheter 22 (FIG. 1) is positioned within the heart using known methods, and ganglionated plexi constituting the target tissue are localized endocardially using high frequency stimulation and observing an immediate vagal response.

Embodiment 7

This embodiment is similar to Embodiment 6, except that the catheter 22 (FIG. 1) is a therapeutic transesophageal probe, positioned within the esophageal lumen. HIFU energy is then directed from the esophagus toward the target tissue under continuous ultrasound imaging guidance.

Embodiment 8

Figure 3:
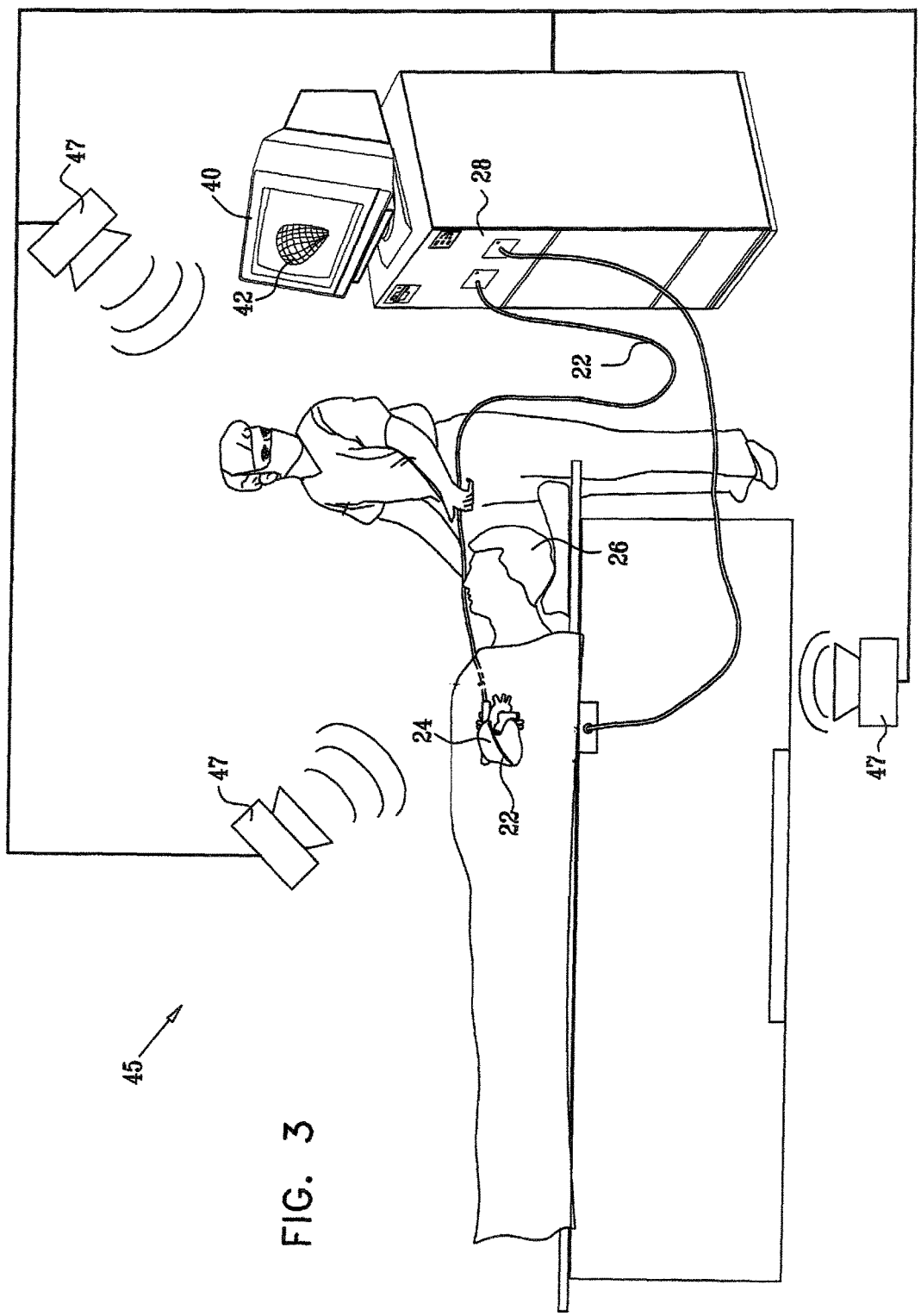
FIG. 3 is an illustration of an ablation system, which is constructed and operative in accordance with an alternate embodiment of the invention.

Reference is now made to FIG. 3, which is an illustration of a system 45, which is constructed and operative in accordance with a disclosed embodiment of the invention. The system 45 is similar to the system 20 (FIG. 1), except that RF transmitters 47 are positioned external to the subject 26, RF energy being directed toward a probe. In this embodiment, the probe, in which is incorporated a resonant circuit (not shown), is used as the catheter 22 (FIG. 1). When an external RF field is generated at the circuit's resonant frequency, RF energy is re-radiated by the probe toward the target tissue. The probe and the transmitters 47 are more fully described in commonly assigned U.S. Patent Application Publication No. 200510101946, which is herein incorporated by reference.

Continuing to refer to FIG. 1, reference is now made to FIG. 4, which is a flow chart of a method of ablation of epicardial neural structures, typically within epicardial fat pads, in accordance with a disclosed embodiment of the invention. It will be understood that the method disclosed herein can alternatively be practiced with any of the other embodiments described above. At initial step 80 the catheter 22 is introduced into the subject 26 and its distal end positioned in the pericardial cavity, using known introduction techniques. The catheter 22 can be placed, for example, using the PerDUCER® Access Device, available from Comedicus Inc., 3989 Central Avenue N.E., Suite 610, Columbia Heights, Minn. 55421.

Next, at step 82, the locations of the epicardial fat pads are accurately determined. Typically, the operator navigates the catheter to one of the known regions where the fat pads are usually located, and then accurately localizes it by using high frequency stimulation. A fat pad location is confirmed by the observation of an immediate vagal response, defined as an increase of at least 50% in R—R interval during atrial fibrillation. This localization technique was described by Nakagawa et al., in Heart Rhythm 2005; 2(5) AB 6-1. Alternatively, if the patient has undergone a previous imaging study, e.g., cardiac CT or MR, preacquired 3-dimensional image data can be imported to the CARTO mapping system. Using the CartoMerge™ module, available from Biosense-Webster, the data is then segmented to represent all four cardiac chambers individually, and the great vessels. During mapping, registration to the 3-dimensional models is accomplished by one or all of the following strategies: manual alignment; landmark pair matching; and surface registration. Once registered, the operator navigates the catheter directly to the predefined fat pads targets or, based on the exact anatomy, to the expected locations of the fat pads. Alternatively, the locations of the fat pads can be determined one-by-one, following ablation of each fat pad.

Next, at step 84 the catheter tip is positioned at an epicardial fat pad to be targeted. If the energy output from the catheter tip is directional, then the orientation of the catheter tip is adjusted so as to direct the energy output at the fat pads. Maximizing the energy delivery to the fat pad reduces unintended damage to tissues other than the fat pad. It may be desirable to introduce coolant via accessory ports (not shown) in the catheter 22 in order to prevent charring of tissue.

Next, at step 86 energy delivery to the fat pad is conducted. As noted above, many different types of ablative energy can be employed in step 86. For example, using the directional ultrasound catheter described above in Embodiment 1, with the catheter tip positioned about 1-3 mm away from the tissue, a burn having a depth of about 8 mm can be obtained using 40 W of power for 120 sec., and irrigation of 10 ml/min. In general, satisfactory results are obtainable with this catheter at 10-45 W, and 0-30 ml/min irrigation.

Control now proceeds to decision step 88, where it is determined whether more epicardial fat pads remain to be ablated. If the determination at decision step 88 is affirmative, then control returns to step 84.

If the determination at decision step 88 is negative, then control proceeds to final step 90. The catheter 22 is withdrawn, and the subject disconnected from the system 20. The procedure terminates.

Additional Applications

There has been substantial research in recent years showing the importance of innervation of the heart by the autonomic nervous system (sympathetic and parasympathetic) in causation and treatment of arrhythmias of various sorts. The methods of the present invention may similarly be applied to perform minimally invasive and noninvasive ablation procedures targeted at other ganglia on the epicardium.

Patients can be classified as sympathetic dominant or parasympathetic dominant. For example, parasympathetic dominant individuals may be identified by neurophysiological testing, such as provocation of syncope during tilt testing. Parasympathetic-dominant individuals may be especially prone to arrhythmias resulting from parasympathetic nerve effects. Fat pad ablation may be prescribed specifically for these individuals in order to treat atrial fibrillation or reduce its occurrence following coronary artery bypass graft (CABG).

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method for ablating epicardial tissue within a body of a subject, comprising the steps of:
   percutaneously inserting a catheter comprising a position sensor at a distal tip into a pericardial cavity of said body;
   locating epicardial target tissue in said pericardial cavity for ablation thereof, wherein said epicardial target tissue is only one epicardial fat pad;
   determining position coordinates of said catheter relative to an epicardial surface of a heart using a control unit and the position sensor, said position coordinates comprising location and orientation information of the distal tip of the catheter;
   displaying said location and orientation information of the distal tip of the catheter relative to the epicardial surface of the heart on a display;
   disposing said catheter in proximity to said only one epicardial fat pad;
   orienting said distal tip of said catheter with respect to said only one epicardial fat pad using a deflection wire coupled to a distal end of said catheter and manipulating a specified surface of an electrode of said distal tip of said catheter against said only one epicardial fat pad using said deflection wire so as to maximize energy transfer from said catheter to said only one epicardial fat pad; and
   directing sufficient energy from said distal tip of said catheter preferentially toward said only one epicardial fat pad to ablate neural structures therein.

2. The method according to claim 1, wherein orienting said catheter comprises sensing location and orientation information thereof and moving said catheter responsively to said information.

3. The method according to claim 1, wherein said energy comprises ultrasound energy.

4. The method according to claim 3, further comprising the step of focusing said ultrasound energy onto said only one epicardial fat pad.

5. The method according to claim 1, wherein said energy comprises laser energy.

6. The method according to claim 1, wherein said energy comprises microwave energy.

7. The method according to claim 1, wherein said catheter comprises a resonant circuit having a resonant frequency; further comprising the steps of:
   generating radiofrequency energy at a site remote from said resonant circuit, at said resonant frequency; and
   re-radiating energy toward said only one epicardial fat pad using said resonant circuit.

8. The method of claim 1, wherein said epicardial target tissue further comprises an epicardial ganglion that is within said only one epicardial fat pad.

9. The method of claim 1, wherein said locating epicardial target tissue in said pericardial cavity comprises using a noninvasive imaging method.

10. A minimally invasive method for ablating epicardial tissue within a body of a subject, comprising steps of:
    percutaneously inserting a catheter comprising a position sensor at a distal tip into a pericardial cavity of said body;
    locating epicardial target tissue in said pericardial cavity for ablation thereof, wherein said epicardial target tissue is only one epicardial fat pad;
    determining position coordinates of said catheter relative to an epicardial surface of a heart using a control unit and the position sensor, said position coordinates comprising location and orientation information of the distal tip of the catheter;
    displaying said location and orientation information of the distal tip of the catheter relative to the epicardial surface of the heart on a display;
    disposing said catheter in proximity to said only one epicardial fat pad;
    orienting said distal tip of said catheter with respect to said only one epicardial fat pad using a deflection wire coupled to a distal end of said catheter so as to maximize energy transfer from said catheter to said only one epicardial fat pad;
    directing sufficient energy from said distal tip of said catheter preferentially toward said only one epicardial fat pad to ablate neural structures therein; and
    manipulating a specified surface of said catheter against said only one epicardial fat pad using said deflection wire for maximizing said energy transfer from said catheter to said only one epicardial fat pad when performing said step of directing sufficient energy from said catheter,
wherein said specified surface includes an exposed surface of a transducer being at said distal tip of said catheter and substantially planar, and wherein said step of orienting said catheter includes manipulating said substantially planar exposed surface of said transducer against said only one epicardial fat pad, wherein said energy transfer is generally perpendicular to said exposed surface of said transducer.

11. The method of claim 10, wherein said epicardial target tissue further comprises an epicardial ganglion that is within said only one epicardial fat pad.

12. The method according to claim 10, wherein said energy comprises ultrasound energy.

13. The method of claim 9, wherein said noninvasive imaging method is selected from the group consisting of cardiac CT, MR imaging, and cardiac neurotransmission imaging.

14. The method of claim 10, wherein said locating epicardial target tissue in said pericardial cavity comprises using a noninvasive imaging method.

15. The method of claim 14, wherein said noninvasive imaging method is selected from the group consisting of cardiac CT, MR imaging, and cardiac neurotransmission imaging.

* * * * *